United States Patent [19]

Chu et al.

[11] Patent Number: 4,899,011

[45] Date of Patent: Feb. 6, 1990

[54] XYLENE ISOMERIZATION PROCESS TO EXHAUSTIVELY CONVERT ETHYLBENZENE AND NON-AROMATICS

[75] Inventors: Yung F. Chu, Cherry Hill, N.J.; Charles T. Kresge, Ellicott City, Md.; Rene B. LaPierre, Medford, N.J.

[73] Assignee: Mobil Oil Corporation, New York, N.Y.

[21] Appl. No.: 819,072

[22] Filed: Jan. 15, 1986

[51] Int. Cl.$^4$ .................................................. C07C 5/27
[52] U.S. Cl. ...................................... 585/481; 585/313
[58] Field of Search ........................ 585/480, 481, 482

[56] References Cited

U.S. PATENT DOCUMENTS

| | | | |
|---|---|---|---|
| Re. 31,782 | 12/1984 | Olson et al. | 585/481 |
| 3,354,078 | 11/1967 | Miale et al. | 208/120 |
| 4,101,595 | 7/1978 | Chen et al. | 585/481 |
| 4,117,026 | 9/1978 | Haag et al. | 260/671 R |
| 4,159,282 | 6/1979 | Olson et al. | 585/481 |
| 4,159,283 | 6/1979 | Nicoletti et al. | 585/481 |
| 4,163,028 | 7/1979 | Tabak et al. | 585/481 |
| 4,278,565 | 7/1981 | Chen et al. | 252/455 |
| 4,312,790 | 1/1982 | Butter et al. | 252/455 |
| 4,375,458 | 3/1983 | Dwyer et al. | 423/329 |
| 4,467,129 | 8/1984 | Iwayama et al. | 585/481 |

FOREIGN PATENT DOCUMENTS 1583707 1/1971 European Pat. Off. .
1581513 3/1978 United Kingdom .

OTHER PUBLICATIONS

Journal of Catalysis, vol. 4, pp. 527-529 (Aug. 1965), by P. B. Weisz and J. N. Miale, entitled "Superactive Crystalline Alumino-Silicate Hydrocarbon Cracking Catalyst".

Journal of Catalysis, vol. 6, pp. 278-287, (1966), by J. N. Miale, N.Y. Chen and P. B. Weisz, entitled "Catalysis by Crystalline Aluminosilicates, IV. Attainable Catalytic Cracking Rate Constants, and Superactivity".

"Catalysis by Crystalline Aluminosilicates: Characterization of Intermediate Pore-Size Zeolites by the 'Constraint Index'" by V. J. Frillette, reprint from Journal of Catalysis, vol. 67, No. 1, Jan. 1981, pp. 218-222.

Primary Examiner—Asok Pal
Attorney, Agent, or Firm—Alexander J. McKillop; Charles J. Speciale; Marina V. Schneller

[57] ABSTRACT

A new xylene isomerization process which is capable of converting ethylbenzene and non-aromatic exhaustively while selectively converting xylenes to thermal equilibrium in mixed EB/xylene feeds is proposed. The new process employs a two component catalyst system; each of the components contains a strong hydrogenation metal and a zeolite. The zeolite of each of the two components differs from the other in its selectivity for xylene isomerization and its capacity to deethylete ethylbenzene. That selectivity for xylene isomerization is described by xylene diffusion properties of the zeolite. In one embodiment of the invention, ZSM-5 of greater than 1 micron crystal size and an alpha value of greater than 100 in a first component and ZSM-5 of less than 1 micron crystal size and an alpha of less than 100 in a second catalyst component satisfy the diffusion properties which allow for the exhaustive conversion of ethyl benzene and non-aromatics and the selectivity for xylene isomerization of typical xylene isomerization feeds. In a preferred embodiment, the feed is cascaded over the first component and then the aforementioned second component.

30 Claims, 3 Drawing Sheets

XYLENE ISOMERIZATION PROCESS TO EXHAUSTIVELY CONVERT ETHYLBENZENE AND NON-AROMATICS

FIELD OF THE INVENTION

A new xylene isomerization process which is capable of converting ethylbenzene and non-aromatics exhaustively while selectively converting xylenes to thermal equilibrium is disclosed. In one embodiment, the new isomerization process employs a xylene isomerization catalyst system based on two platinum-containing zeolite compositions.

BACKGROUND OF THE INVENTION

Xylenes are valuable industrial chemicals. Xylenes are derived primarily from aromatic naphthas such as petroleum reformates and pyrolysis gasolines. Petroleum reformates result from processing petroleum naphthas over a catalyst such as platinum on alumina at temperatures which favor dehydrogenation of naphthenes. Pyrolysis gasolines are liquid products resulting from steam cracking of hydrocarbons to manufacture ethylene, propylene, and the like.

Generally, regardless of the aromatic naphtha source, it has been the practice to subject the liquid hydrocarbon to extraction with a solvent highly selective for aromatics to obtain an aromatic mixture of the benzene and alkylated benzenes present in the aromatic naphtha. The resulting extract can then be distilled to separate benzene, toluene and $C_8$ aromatics from higher boiling compounds in the extract. Benzene and toluene are recovered in high purity; however, the $C_8$ fraction, containing valuable para-xylene, is a mixture of three xylene isomers with ethylbenzene. These mixtures will also contain $C_8$–$C_9$ paraffins, the amount of which is determined both by the source of the naphtha as well as the efficiency of the solvent extraction.

As commercial use of para- and ortho-xylene has increased, there has been interest in isomerizing the xylene isomers toward an equilibrium mix and thus increasing yields of the desired xylenes. Of the xylene isomers, i.e., ortho-, meta- and para-xylene, meta-xylene is the least desired product, while ortho- and para-xylene are the most desired products. Para-xylene is of particular value as it is useful in the manufacture of terephthalic acid which is an intermediate in the manufacture of polyesters, and of synthetic fibers such as "Dacron".

In practice, isomerization processes are operations used in conjunction with xylene separation processes. A virgin $C_8$ aromatics mixture is fed to such a combined process system, along with undesired isomers emerging from the product separation steps. The feed is charged to the isomerizing unit and the effluent isomerizate $C_8$ aromatics are sent to the product separation steps. The composition of isomerizer feed is then a function of the virgin $C_8$ aromatic feed, the product separation unit performance, and the isomerizer performance. The objective in the isomerization reactor is to bring the charge as near to the equilibrium concentration as may be feasible consistent with reaction times which do not give extensive cracking and disproportionation. The thermodynamic equilibrium varies slightly with temperature.

The rate of ethylbenzene conversion in a $C_8$ aromatic mixture is related to effective contact time. Hydrogen partial pressure can have a very significant effect on ethylbenzene conversion. Products formed from ethylbenzene include $C_8$ naphthenes, benzene from hydrocracking ethylbenzene and $C_9+$ aromatics from disproportionation, as well as total loss to other than $C_8$ molecular weight components, such as $C_5$ and lighter hydrocarbon byproducts.

By comparison, the three xylenes isomerize much more selectively than does ethylbenzene. However, the xylenes do exhibit different rates of isomerization and hence, with different feed composition situations, the rates of approach to equilibrium vary considerably. Loss of xylenes to other molecular weight products varies with contact time. By-products include naphthenes, toluene, $C_9$ and heavier aromatics and $C_5$ and lighter hydrocracking products.

Because of the deleterious effects of ethylbenzene build up in the loop manufacture of the xylenes and because of the great expense of removing it from mixed $C_8$ aromatics, a process which would result in ethylbenzene conversion at a rate approaching that of xylene isomerization would be desirable provided xylene losses can be maintained at a reasonable level. Progress toward such a goal was heralded by U.S. Pat. No. 4,163,028 which describes a catalyst and its use in an isomerization process conducted at 800° to 1000° F.; the catalyst described in 4,163,028 comprises a zeolite having a constraint index of about 1 to 12 and having a silica/alumina ratio of at least 500. An improved catalyst for that aforementioned goal was later described in U.S. Pat. No. 4,312,790.

However, even the use of catalysts of U.S. Pat. Nos. 4,163,028 and 4,312,790 can result in unacceptively high xylene losses. For example, we have determined that catalysts of U.S. Pat. Nos. 4,163,028 and 4,312,790 give unacceptably high xylene losses when xylene isomerization feeds containing greater than 15% ethylbenzene are processed under conditions which give greater than about 50% conversion of ethylbenzene per pass; that situation can be further aggravated if the isomerization feed contains paraffins. The catalyst system of the present invention does not suffer from these limitations.

SUMMARY OF THE INVENTION

The process of the invention is directed to exhaustively converting ethylbenzene and non-aromatics in mixed ethylbenzene xylene containing feeds, while simultaneously converting xylenes to thermal equilibrium. By exhaustively converting ethylbenzene and non-aromatics, we mean that per pass at least half the ethylbenzene is deethylated and at least a third of the non-aromatics, paraffins, are hydrocracked without excessive loss of xylenes to heavier aromatics. In this way, the volume of the recycle stream and/or complexity of the separation processes are minimized by excessive loss of xylenes to heavier aromatics. We mean that at 50% ethylbenzene conversion, the amount of $C_9+$ aromatics produced is greater than 2 wt % of the $C_8$ feed.

This new process comprises contacting an isomerization feed containing $C_8$ aromatics and paraffins, with an improved catalyst system, under conversion conditions including a temperature of from about 400°-1000° F., a pressure of from about 0-1000 psig, a WHSV of between 0.5 and 100 and a $H_2/H_C$ molar ratio of between about 0.5 and 10. Preferably, those conditions include a temperature of from about 750° to 900° F., a pressure of from about 50 to 400 psig, a WHSV of between 3 and 50 and $H_2/H_C$ molar ratio of between about 1 and 5.

The new catalyst system is a two component system. One of the two components selectively converts ethylbenzene to benzene and ethane and hydrocracks paraffins. The other component of the catalyst system isomerizes the xylenes to effect isomerization to the extent that the amount of para-xylene in the isomerization product effluent is at least that at the thermal equilibrium of the xylene(s). In one embodiment of the process, the component of the catalyst system effective for converting the ethylbenzene in the mixed xylenes will show reduced activity for isomerization of the xylenes. Each of the zeolite catalysts contains an amount of a noble metal effective to increase the hydrogenative activity of the zeolite. Two component catalyst system which converts ethylbenzene in a mixed xylene feed by transalkylation is described in U.S. Pat. No. Re. 31,782.

DETAILED DESCRIPTION OF THE INVENTION

Xylene Isomerization Feeds

Xylene isomerization feeds, processed in accordance with the invention, are any aromatic $C_8$ mixture containing ethylbenzene and xylene(s). Generally, such a mixture will have an ethylbenzene content in the approximate range of 5 to 60 weight %, and ortho-xylene content in the approximate range of 0 to 35 weight %, a meta-xylene content in the approximate range of 20 to 95 weight %, and a para-xylene content in the approximate range of 0 to 15 weight %. Other xylene isomerization processes which also operate to convert the ethylbenzene in the isomerization feed operate with and require high ethylbenzene content in the feed and thus involve ethylbenzene and naphthene recycle to maintain high ethylbenzene content in the isomerization feed. The feed in addition to the above aromatic $C_8$ mixture can contain non-aromatic hydrocarbons, such as paraffins and naphthenes. The paraffins will comprise 0 to 20 weight percent of the feed; generally, the paraffins will comprise $C_8$–$C_9$ paraffins.

Process Conditions of Catalytic isomerization of Xylenes

In accordance with the invention such a feed is contacted with a catalyst system under conversion conditions. These conversion conditions include a temperature of from about 400°-1000° F., a pressure of from about 0-1000 psig, a WHSV of between 0.5 and 100 and a $H_2/H_C$ molar ratio of between about 0.5 and 10. Preferably, those conditions include a temperature of from about 750° to 900° F., a pressure of from about 50 to 400 psig, a WHSV of between 3 and 50 and $H_2/H_C$ molar ratio of between about 1 and 5.

The catalyst system used in accordance with the invention is multifunctional. One function of the catalyst system is to effect isomerization of the xylene components to thermal equilibrium, while another function of the catalyst system is to deethylate ethylbenzene (and to crack paraffins).

To effect exhaustive conversion of ethylbenzene and non-aromatics, while bringing the xylene components of $C_8$ feed to thermal equilibrium the isomerizer without excessive loss of xylenes to heavier aromatics, the feed must be contacted with the two component catalyst system, under conversion conditions described above. The conversion process described herein may be carried out as a batch type, semi-continuous or continuous operation. After use in a moving bed reactor, the catalyst can be regenerated, in a regeneration zone in which coke is burned from the catalyst in an oxygen containing atmosphere, e.g., air at an elevated temperature after which the regenerated catalyst is recycled to the conversion zone for further contact with the charge stock. In a fixed bed reactor, regeneration can be carried out in a conventional manner by using initially an inert gas containing a small amount of oxygen (0.5-2%) to burn coke in a controlled manner so as to limit the temperature to a maximum of around 500°-550° C.

In general, the xylene isomerization reaction is carried out in a fixed bed flow reactor containing the catalyst system described above. In a preferred embodiment the two components of the catalyst system are in sequential beds. That is, the component of the catalyst system used in the process of the invention which is effective to isomerize the xylene components forms one part of the bed, while the other component of the catalyst system forms the remaining portion of the catalyst bed. Thus, in theory, the conversion process of the invention could be carried out in two different reactors. However, preferably, the feed is cascaded over the catalyst system disposed in the reactor in sequential beds. In cascading, the feed is contacted with the two components of the catalyst system without intervening separation of light gases.

In embodiments below, the component of the catalyst system effective to hydrocrack paraffins, and to deethylate ethylbenzene is upstream with respect to the catalyst component which is effective to isomerize the xylene components of the $C_8$ aromatic feed. In this embodiment, the catalyst component which is effective to deethylate ethylbenzene is employed in a volume which is at most one-half ($\frac{1}{2}$) of the bed volume and most preferably it is employed in a volume not greater than the one-third ($\frac{1}{3}$) the volume of the catalyst bed. For example, the catalyst component to deethylate ethylbenzene may comprise 25 percent of the bed volume while the xylene isomerization component comprises 75 percent of the bed volume.

After the conversion process the isomerization product can be treated to isolate para-xylene. Thus, the isomerizate product can be fed to a crystallizer to crystallize para-xylene and thus the para-xylene can be isolated. The residual isomerizate can then be stripped of products lighter than $C_8$. Products heavier than $C_9$ in the residual isomerizate can be further processed. $C_8$ fractions from which para-xylene has been removed can be recycled to the isomerizer.

One result of the process of the invention is to convert the mixed xylene components of the feed containing p-xylene in an amount less than that at thermal equilibrium to an extent such that product effluent from the isomerizer contains p-xylene in an amount at least approaching that of p-xylene in the xylene mixture produced at thermal equilibrium. Another result of the process of the invention is exhaustive conversion of ethyl benzene, i.e. at least 50% conversion of ethyl benzene in the feed which is isomerized.

Thus, in accordance with the invention, ethyl benzene conversion during the isomerization surpasses that possible by prior isomerization processes. Moreover, xylene yields are at least comparable and most often greater than those of prior isomerization processes as a result of lower losses to $C_9+$ aromatics.

Catalyst Composition for Process

The foregoing results of the invention are realized by undertaking the isomerization in the presence of multifunctional catalyst composition. The catalyst composition comprises two components.

Each of those two components is characterized by two common factors. Each contains a strong hydrogenation/dehydrogenation component and each comprises a zeolite which is characterized by a constraint index within the approximate range of 1 to 12. Zeolites having a constraint index within the approximate range of 1 to 12 are often grouped as members of the class of zeolites referred as shape selective.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the acid catalyzed cracking rate constants for the two hydrocarbons. The ZSM-5 zeolite has a constraint index of about 8.3 at about 600° F. Constraint Index (CI) values for some other zeolites are:

| Zeolite | C.I. |
|---|---|
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that these are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite, may affect the constraint index. It will accordingly be understood by those skilled in the art that the constraint index, as utilized herein, while affording a highly useful means for characterizing the zeolites of interest is an approximation, taking into consideration the manner of its determination, with probability, in some instances, of compounding variable extremes.

While the above experimental procedure for determining the constraint index will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

Generally, the zeolite, either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

As indicated above each of the two catalyst components is a zeolite which is associated with a hydrogenation-dehydrogenation component. The hydrogenation component is preferably a noble metal such as platinum, palladium, or another member of the platinum group such as rhodium with platinum most preferred. Combinations of noble metals such as platinum-rhenium, platinum-palladium, platinum-iridium or platinum-iridium-rhenium together with combinations with non-noble metals, particularly of Groups VIA and VIIIA are of interest, particularly with metals such as cobalt, nickel, vanadium, tungsten, titanium and molybdenum, for example, platinum-tungsten, platinum-nickel or platinum-nickel-tungsten.

The foregoing metals may be incorporated into the catalyst by any suitable method such as impregnation or exchange onto the zeolite. The metal may be incorporated in the form of a cationic, anionic or neutral complex such as $Pt(NH_3)_4^{2+}$ and cationic complexes of this type will be found convenient for exchanging metals onto the zeolite. Anionic complexes such as the vanadate or metatungstate ions are useful for impregnating metals into the zeolites. Incorporation is preferably undertaken in accordance with the invention of U.S. Pat. No. 4,312,790.

The amount of the hydrogenation-dehydrogenation component is suitably from 0.01 to 10 percent by weight, normally 0.1 to 5 percent by weight, although this will, of course, vary with the nature of the component, less of the highly active noble metals, particularly platinum, being required than of the less active base metals.

The two components of the catalyst system of the invention differ from each other in two significant respects. Each will be characterized by different acidities and each will be characterized by different xylene diffusion properties.

In the embodiments described below, the acidity of the zeolite will be expressed as its alpha value. The test for alpha value determination is further described in a letter to the editor, entitled "Superactive Crystalline Alumino-Silicate Hydrocarbon Cracking Catalyst", by P. B. Weisz and J. N. Miale, *Journal of Catalysis*, Vol. 4, pp. 527–529 (August 1965) and in U.S. Pat. No. 3,355,078. The entire contents of both are expressly incorporated by reference herein. A procedure for determining the alpha value was more recently described in the *Journal of Catalysis*, Vol. VI, page 278–287, 1966, which is incorporated by reference herein.

Each of the components of the catalyst system will exhibit mutually exclusive xylene diffusional properties.

Those properties can be identified by noting the time (in minutes) required to sorb 30% of the equilibrium capacity of ortho xylene at 120° C. and at an o-xylene partial pressure of 4.5±0.8 mm of mercury, a test described by Olson et al in U.S. Pat. Nos. 4,117,026, 4,159,282 and Re. 31,782, each of which is incorporated by reference herein. Herein, that equilibrium capacity of orthoxylene is defined as greater than 1 gram of xylene(s) per 100 grams of zeolite. In accordance with the invention, the deethylation component will have a value (in minutes) in excess of about 50 and preferably greater than 100 but less than 10,000 minutes while on the other hand, the isomerization component will require o-xylene sorption times of less than about 50 minutes and preferably less than 10 minutes.

The alpha value of the zeolite of the component of the catalyst system which is effective to deethylate ethylbenzene to produce benzene and ethane/ethene, as well as to hydrocrack nonaromatics present, will be at least 100. Generally, the alpha value of that component ranges from 100 to 500, and preferably it ranges from 100 to 300. The xylene diffusion properties of this component is such that under the process conditions, described above, deethylation is favored over isomerization. As pointed out above, the zeolite of this component of the catalyst system is one characterized by a constraint index within the approximate range of 1 to 12. This parameter embraces a number of zeolites some of which are defined above. When, as in an embodiment described below, the zeolite of this component of the catalyst system is ZSM-5, the requisite diffusion properties are satisfied by providing ZSM-5 in crystals, the minimum dimension of which is at least $1\mu$ (one micron). Production of ZSM-5 with a crystal size, the minimum dimension of which is at least $1\mu$ is described in, for example, U.S. Pat. No. 4,375,458, G.B. No. 1,581,513, E.P.O. Publication Nos. 0026962 and 0026963. Moreover, use of the same has been described for xylene isomerization processes in, e.g., U.S. Pat. No. 4,278,565 and Re 31,782, each of which is incorporated by reference herein. If the zeolite of requisite constraint index is other than ZSM-5, the foregoing ZSM-5 crystal size requisite to satisfy the xylene diffusion properties to produce the result of selective deethylation may be inappropriate.

The other component of the catalyst system is effective to isomerize the xylenes of the feed containing $C_8$ aromatics. This component of the catalyst system will comprise ZSM-5. The acidity of the ZSM-5 of this component, expressed as the alpha value, will be less than 100. Preferably, the ZSM-5 will have an alpha value of at most 50; and preferably, the alpha value will range from 5 to 25. The minimum dimension of crystals of ZSM-5 used in this component will be less than $1\mu$, as determined by election microscopy, and generally less than $0.5\mu$. Preferably, that minimum dimension of ZSM-5 is at most $0.10\mu$; and most preferably that minimum dimension will range from about 0.02 to $0.05\mu$.

In practicing the process of the invention, it may be desirable to formulate the catalyst system of the invention with another material resistant to the temperature and other conditions of the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families includes the sub-bentonites and the kaolins commonly known as Dixie, McNamee:-Georgia and Florida clays or others in which the main mineral constituent is halloysite, kaolinite, dickite, nacrite or anauxite. Such clays can be used in a raw state as originally mined or initially subjected to calcination acid treatment or chemical modification.

In addition to the foregoing materials, the zeolite employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The following examples are illustrative of the process of the invention.

EXAMPLES

General Preparative Procedure for Catalysts A–E

Extrudate samples which consist of 1/16 in. diameter particles of 65 wt % Na-form ZSM-5/35 wt % binder alumina are processed to convert the inert sodium form of the zeolite into the active hydrogen or acid form. The conversion procedure consists of calcining the samples at 1000° F. The acid zeolite-containing extrudates are then impregnated with a platinum salt to the desired Pt loading. In a preferred embodiment this is accomplished by evacuating the air from the extrudate sample and replacing the air with $CO_2$. An aqueous solution of $H_2PtCl_6$, containing the equivalent of 0.3 wt % Pt, is introduced to the $CO_2$ saturated samples. The samples are then dried at about 250° F. and calcined at 900° F. in air. The $CO_2$ treatment may not be necessary.

Catalyst A: 0.3 wt % Pt, 1/16 in. dia., 65 wt % HZSM-5/35 wt % binder alumina. The minimum dimension of the ZSM-5 crystal in this example is approximately 2.5 to $4\mu$. The extrudate catalyst has about 200 alpha before Pt impregnation.

Catalyst B: 0.3 wt % Pt, 1/16 in. dia., 65 wt % HZSM-5/35 wt % binder alumina. The minimum dimension of the ZSM-5 crystal in this example is approximately 1–$2\mu$. The extrudate catalyst has about 200 alpha before Pt impregnation.

Catalyst C: 0.3 wt % Pt, 1/16 in. dia., 65 wt % HZSM-5/35 wt % binder alumina. The minimum dimension of the ZSM-5 crystal in this example is approximately 0.02 to $0.05\mu$. The extrudate catalyst has about 200 alpha before Pt impregnation.

Catalyst D: Equivalent of Catalyst A without platinum.

Catalyst E: An aqueous solution of $[Pt(NH_3)_4]Cl_2$ containing the equivalent of 0.1 wt % Pt is added to a 50/50 mixture of NaZSM-5 (minimum dimension 0.02 to $0.05\mu$) and binder alumina. This Pt-containing mixture is extruded to form 1/16 in. diameter particles. The extruded material is then calcined in nitrogen at 1000° F., ammonium ion exchanged, and calcined in air at 1000° F. The calcined extrudates are then treated with steam at 1025° F. for 24 hours. The catalyst thus made has about 10 alpha.

In all the examples, unless otherwise stated, the second catalyst is always a conventional catalyst, specifically catalyst E above, of which both Pt and the zeolite extrudates have been severely steamed to reduce the acidity of the catalyst and it represents ⅔ of the total catalyst loading. ZSM-5 samples having crystals sizes the minimum dimensions of which range from 0.02 to 0.05μ can be prepared by the following procedure. A sodium silicate solution was prepared by mixing 16 parts water and 27.7 parts sodium silicate (28.7 wt. % $SiO_2$, 8.9 wt. % $Na_2O$, 62.4 wt. % $H_2O$) followed by addition of 0.08 parts Daxad 27 (W. R. Grace Chemical Division). The solution was cooled to approximately 15° C.

An acid solution was prepared by adding 1 part aluminum sulfate (17.2 wt. % $Al_2O_3$) to 16.4 parts water followed by 2.4 parts sulfuric acid (93 wt. % $H_2SO_4$) and 1.2 parts NaCl.

These solutions were mixed in an agitated vessel while 3.9 parts of NaCl were added. The molar ratios expressed as oxides were as follows in the resultant mixture:

$SiO_2/Al_2O_3 = 78.5$
$Na_2O/Al_2O_3 = 49.5$

The gel was then heated to about 93° C., agitation was reduced and an organic solution containing 0.8 parts n-propyl bromide and 1.5 parts methyl ethyl ketone was added above the gel. After these organics were added, 2.3 parts of n-propyl amine was added to the organic phase above the gel. This mixture was held at about 93° C. for 6 hours, then severe agitation was resumed. Crystallization was conducted at 93°–99° C. until the gel was 80% crystallized, at which time temperature was increased to 150°–160° C. Unreacted organics were removed by flashing and the remaining contents cooled. The zeolite slurry product was diluted with 4–5 parts water per part slurry and 0.0002 parts of flocculent (Rohm and Haas, Primafloc C-7) per part slurry, and allowed to settle. Supernant liquid was drawn off. The settled solids were reslurried to the original volume of the preceeding step with water and 0.00005 parts of flocculent per part slurry. After settling, the aqueous phase was decanted. This was repeated until the sodium level of the zeolite was less than 0.10 wt. %. Then 0.1 parts ammonium nitrate per part slurry were added to the settled solids and the water from the previous decantation. The mixture was reslurried and the solids were allowed to settle. The washed zeolite solids were filtered identified as ZSM-5 by X-ray diffraction, and analyzed as having a $SiO_2/Al_2O_3$ mole ratio of 62.6 and a sodium content of 0.02 wt. % (dry basis). The minimum dimensions of the crystals of ZSM-5 produced thereby ranged from 0.02 to 0.05μ. The reactor used is a fixed-bed reactor. The catalysts were all pretreated in $H_2$ at 200 psig and 900° F. for about 2 hours before liquid was charged into the reactor. The charge stocks tested consist of 8–40% EB and 0–3% $C_9$ paraffins with the balance meta rich mixed xylenes.

EXAMPLE 1

Without cascading with catalyst E, catalyst A showed insufficient p-xylene conversion activity, even though high EB conversion and low xylene loss are achieved (see Table 1).

In Table 1, isomerizations were undertaken using catalyst A alone, under various isomerization conditions.

TABLE 1

| | | | |
|---|---|---|---|
| Temperature, °F. | | 800 | 800 | 800 |
| Pressure, PSIG | | 200 | 200 | 400 |
| WHSV | | 2.9 | 8.6 | 8.7 |
| $H_2$/HC Molar Ratio | | 2.9 | 3.0 | 3.0 |
| Time on Stream, Hrs. | | 3.5 | 9.5 | 16.0 |
| EB Conversion, Wt % | | 99.6 | 99.6 | 99.0 |
| Xylene Loss, Wt % | | 13.9 | 4.8 | 13.9 |
| Equilibrium Approach, % | | | | |
| P-Xylene | | 62.7 | 49.4 | 54.0 |
| HC Prod Dist, Wt % | | | | |
| | Feed | | | |
| $C_1$–$C_4$ N.A. | | 14.0 | 12.8 | 17.1 |
| $C_5$–$C_7$ N.A. | | 1.9 | 2.6 | 10.5 |
| $C_8$ Naphthene | | 0.3 | 0.6 | 3.9 |
| $C_9$ Naphthene | | 0.0 | 0.1 | |
| Benzene | 0.1 | 20.9 | 24.0 | 13.8 |
| Toluene | 1.2 | 13.6 | 5.4 | 5.7 |
| EB | 41.2 | 0.2 | 0.3 | 0.4 |
| P-Xylene | 5.9 | 9.1 | 9.1 | 8.4 |
| M-Xylene | 38.6 | 27.9 | 32.6 | 28.6 |
| O-Xylene | 13.0 | 12.0 | 12.5 | 11.4 |
| $C_9$+ Arom. | | 0.3 | 0.1 | 0.2 |
| Total | 100.0 | 100.0 | 100.0 | 100.0 |

After cascaded by catalyst E, the process produced thermal equilibrium amount of p-xylene along with significantly higher EB conversion and better xylene selectivity. The following example shows that using the two-catalyst system the process can handle essentially all kinds of mixed xylene feedstocks.

EXAMPLE 2

Table 2 shows that catalysts A and E together are better than catalyst E alone for three different kinds of mixed xylene feeds. Charge stock 1 represents an extracted feed which contains low (i.e. 8%) EB (ethylbenzene), about 9% p-xylene, 62% m-xylene and about 20% o-xylene. Charge stock 2 represents a non-extracted feed derived from reformate heart-cut which typically contains about 3% $C_9$ paraffins, 20% EB, 1% p-xylene, 52% m-xylene and 25% o-xylene. Charge stock 3 represents a high EB feed typically obtained from pyrolysis gasoline which contains about 40% EB, 6% p-xylene, 40% m-xylene and 13% o-xylene.

TABLE 2

EFFECT OF VARIOUS FEEDS

| Charge Stock | 1 | 1 | 2 | 2 | 3 | 3 |
|---|---|---|---|---|---|---|
| Catalyst | A/E | E | A/E | E | A/E | E |
| EB Conversion, Wt % | 76 | 30 | 85 | 30 | 85 | 40 |
| Xylene Loss, % | 1.1 | 1.0 | 0.5 | 1.0 | 3.5 | 5.4 |
| P-Xylene Equil. Appr. | 103 | 103 | 102 | 103 | 103 | 104 |
| $C_9$ Conversion, Wt % | — | — | 77 | 20 | — | — |

Conversion Condition: 800° F., 200 psig, 9 WHSV and 3/1 $H_2$/HC

EXAMPLE 3

Figure 1:
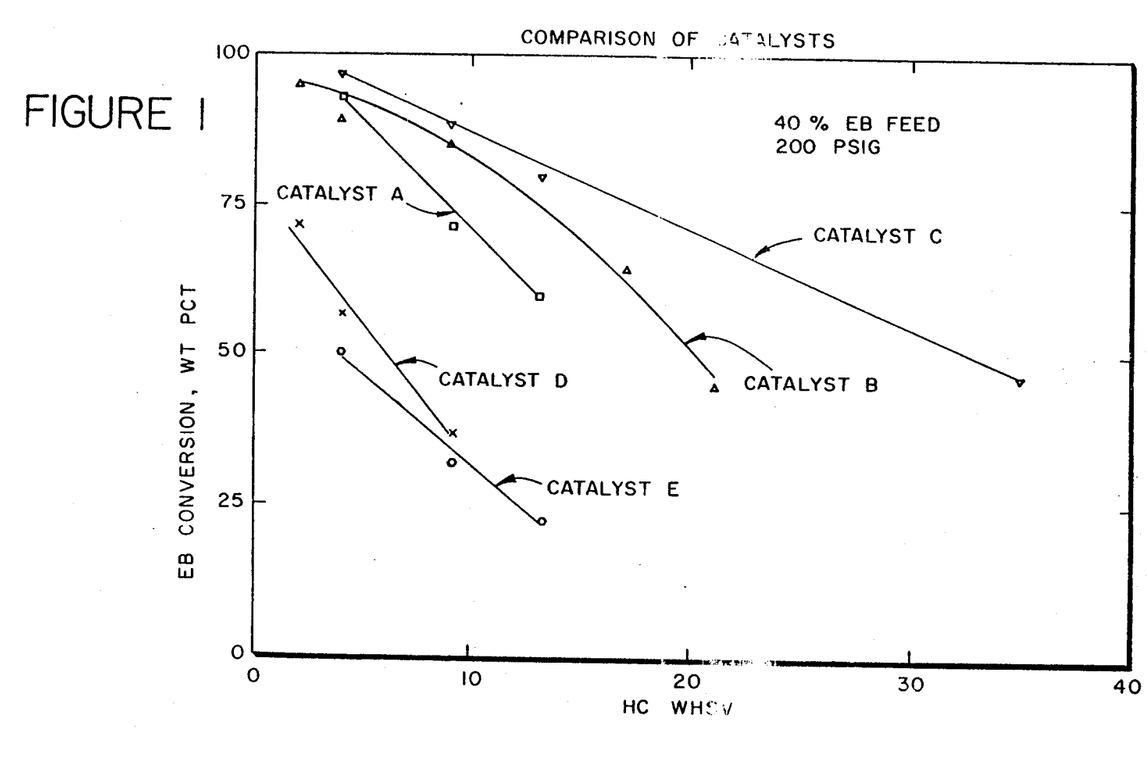
FIG. 1 is a graph of ethylbenzene (EB) conversion in weight percent plotted against HC WHSV, for various catalysts described in the Examples.
Figure 2:
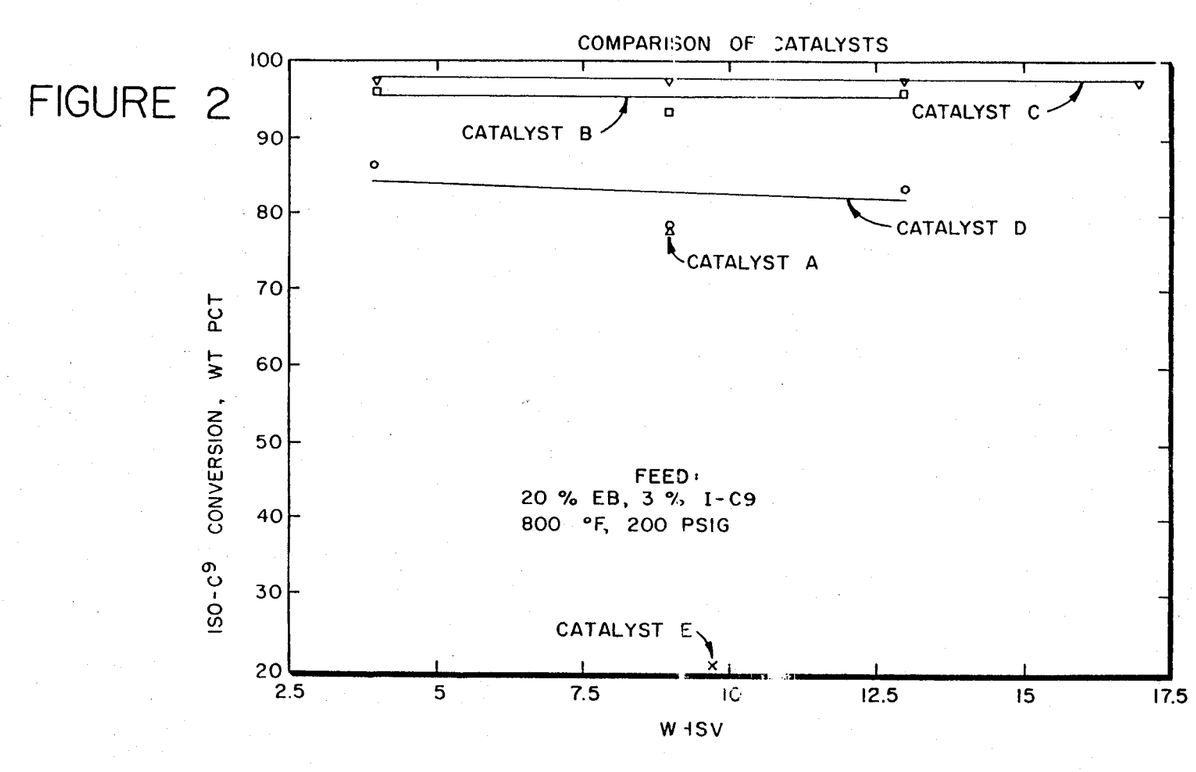
FIG. 2 is a graph of $C_9$ conversion in weight percent plotted against WHSV.
Figure 3:
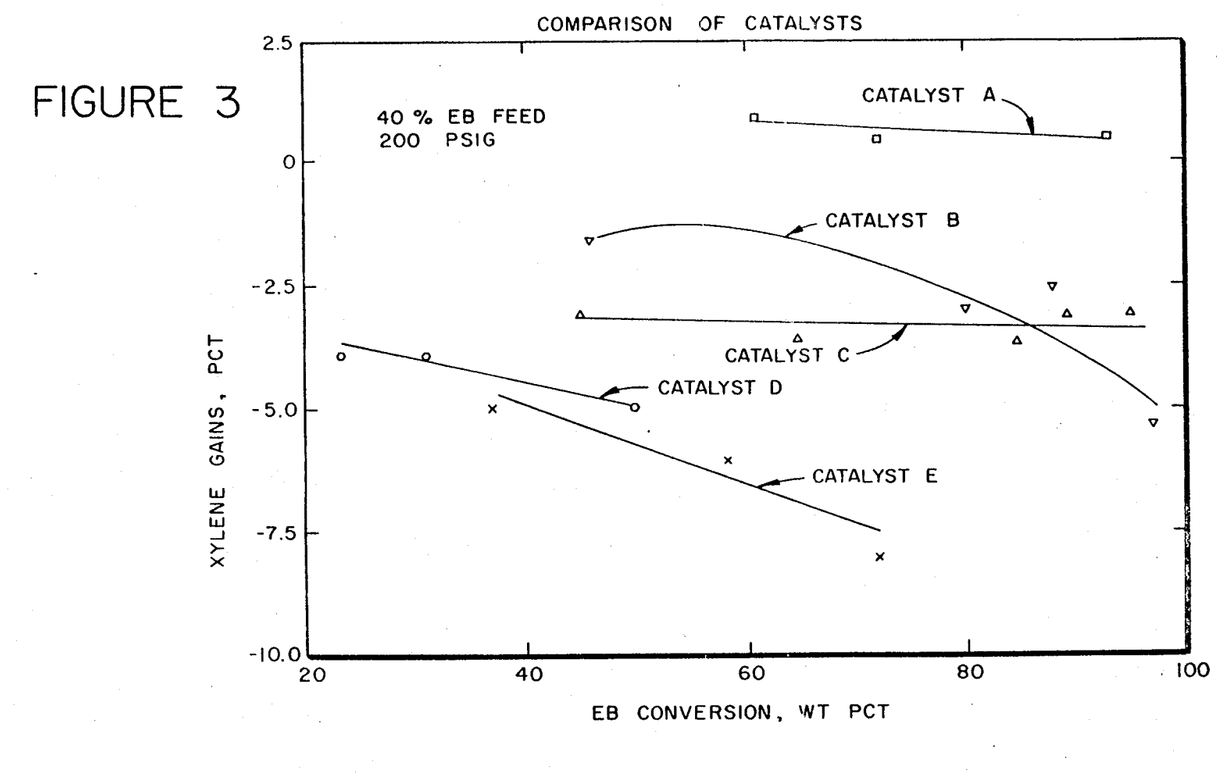
FIG. 3 is a graph of xylene gains, in weight percent, plotted against EB conversion in weight percent.

Three different crystal size ZSM-5 catalysts (catalysts A, B and C) were evaluated. The two-catalyst system is better than the catalyst system consisting of catalyst E alone. It is also clear that even though the smaller crystal size ZSM-5 (i.e. catalyst C) is more active than the larger crystal size ZSM-5 (i.e. catalysts A and B) in both EB and paraffin conversions (see FIGS. 1 and 2), xylene selectivity is however better for the larger crystal size ZSM-5 catalysts (see FIG. 3).

In the foregoing examples, a catalyst system used at the top of the catalyst bed replacing a part of the catalyst E resulted in dramatic isomerization production advantages.

The specific results described herein were obtained by replacing at most one-third (⅓) of catalyst E from the top of the catalyst bed. The new process can be easily implemented in existing isomerization units without hardware changes.

We claim:

1. A process for isomerizing a feed which contains 0–20 weight percent paraffins and an aromatic $C_8$ mixture of ethylbenzene and xylene in which the para-xylene is less than that at thermal equilibrium which process comprises contacting the feed, under isomerization conditions, with a two component catalyst system including component (1) and component (2) wherein component (1) comprises a zeolite of a constraint index of about 1 to about 12 and of an ortho-xylene sorption time of greater than 50 minutes based on its capacity to sorb 30% of the equilibrium capacity of ortho xylene at 120° C. and at an ortho xylene partial pressure of 4.5±0.8 mm of mercury and 0.05 to 10 wt % of a hydrogenation component and is effective, under said isomerization conditions, to deethylate benzene; and component (2) comprises a zeolite, having a constraint index within the approximate range of 1 to 12 and characterized by a xylene sorption capacity greater than 1 gram/100 grams of zeolite and an ortho-xylene absorption time for 30 percent of said capacity of less than 10 minutes, where the sorption capacity and sorption times are measured at 120° C. and a xylene pressure of 4.5±0.8 mm of mercury; and comprises 0.05 to 10 weight percent of a hydrogenative component wherein the amount of component (2) in the catalyst system is at least 50 percent by volume of the catalyst system wherein isomerization conditions include a temperature of from about 400° to 1000° F., a pressure of from about 0 to 1000 psig, a WHSV of between 0.5 and 100 and a $H_2/HC$ molar ratio of between about 0.5 and 10; and whereby the ethylbenzene content of the feed is exhaustively converted, wherein exhaustively converted is deethylation of at least half the ethylbenzene and includes hydrocracking of at least one-third of said 0–20 weight percent of paraffins.

2. The process of claim 1, wherein the feed is contacted with component (1) of the catalyst system before the feed is contacted with component (2) of the catalyst system.

3. The process of claim 2, wherein the catalyst system is a fixed bed catalyst system.

4. The process of claim 3, wherein component (1) and component (2) are in sequential beds in the fixed bed catalyst system.

5. The process of claim 1, wherein said hydrogenative component of each of component (1) and component (2) is platinum.

6. The process of claim 1, wherein said feed contains 0 to 20 weight percent non-aromatics and wherein component (1) is effective to hydrocrack said non-aromatics.

7. The process of claim 1 wherein the alpha value of the zeolite of component (1) ranges from 100 to 500.

8. The process of claim 1 wherein the alpha value of the zeolite of component (2) is less than 50.

9. The process of claim 7, wherein the alpha value of the zeolite of component (2) is less than 50.

10. A process for isomerizing a feed which contains 0–20 weight percent paraffins and an aromatic $C_8$ mixture of ethylbenzene and xylene in which the para-xylene is less than that at thermal equilibrium, which comprises contacting the feed, under isomerization conditions, with a two component catalyst system comprising component (1) and component (2) wherein component (1) comprises a zeolite of a constraint index of about 1 to about 12 and of an ortho-xylene sorption time of greater than 50 minutes based on its capacity of sorb 30% of the equilibrium capacity of ortho-xylene at 120° C. and an ortho xylene partial pressure of 4.5±0.8 mm of mercury and 0.05 to 10 wt % of a hydrogenation component and is effective, under said isomerization conditions, to deethylate benzene, and component (2) comprises ZSM-5 and a metal which is a strong hydrogenative, wherein ZSM-5 has a crystal size the minimum dimension of which ranges up to about 0.10μ, and wherein said ZSM-5 is characterized by an alpha value of less than 100, wherein the metal comprises 0.01 to 10 weight percent of component (2); wherein the amount of component (2) in the catalyst system is at least 50 percent by volume of the catalyst system wherein isomerization conditions include a temperature of from about 400° to 1000° F., a pressure of from about 0 to 1000 psig, a WHSV of between 0.5 and 100 and a $H_2/HC$ molar ratio of between about 0.5 and 10; and whereby the ethylbenzene content of the feed is exhaustively converted;

wherein exhaustively converted is deethylation of at least half the ethylbenzene and includes hydrocracking of at least one-third of said 0–20 weight percent of paraffins.

11. The process of claim 10, wherein the feed is contacted with component (1) of the catalyst system before the feed is contacted with component (2) of the catalyst system.

12. The process of claim 11, wherein the catalyst system is a fixed bed catalyst system.

13. The process of claim 12, wherein component (1) and component (2) are in sequential beds in the fixed bed catalyst system.

14. The process of claim 10, wherein each of component (1) and component (2) comprises 0.01 to 10 weight percent platinum.

15. The process of claim 10, wherein component (2) comprises 1 to 90 percent by weight binder material.

16. The process of claim 14, wherein component (2) comprises 1 to 90 percent by weight binder material.

17. The process of claim 10, wherein the alpha value of component (1) is 100 to 500.

18. The process of claim 10, wherein the alpha value of component (2) is less than 50.

19. The process of 17, wherein the alpha value of component (2) is less than 50.

20. The process for isomerizing a feed which contains 0–20 weight percent paraffins and ethylbenzene and xylene, in which the para-xylene is less than that at thermal equilibrium of the mixture of ortho-, meta- and para-xylene contained in the feed, which comprises contacting the feed under isomerization conditions with a two component catalyst system comprising component (1) and component (2) wherein component (1) comprises ZSM-5, and a metal which is a strong hydrogenative metal, wherein the ZSM-5 has a crystal size the minimum dimension of which is greater than 1μ and wherein ZSM-5 has an alpha value greater than 100, and wherein the metal comprises about 0.01 to about 10 weight percent of component (1); and component (2) comprises a zeolite and a hydrogenative metal, wherein said zeolite has a constraint index within the approximate range of 1 to 12 and which is characterized by a xylene sorption capacity greater than 1 gram/100 grams of zeolite and an ortho-xylene sorption time for 30 percent of said capacity of than 10 minutes, where the sorption capacity and sorption times are measured at 120° C. and a xylene pressure of 4.5±0.8 mm of mercury wherein component (2) comprises at least 50 percent by volume of the catalyst system.

wherein isomerization conditions include a temperature of from about 400° to 1000° F., a pressure of from about 0 to 1000 psig, a WHSV of between 0.5 and 100 and a $H_2$/HC molar ratio of between about 0.5 and 10;

whereby the ethylbenzene content of the feed is exhaustively converted, wherein exhaustively converted is deethylation of at least half of the ethylbenzene and includes hydrocracking of at least one-third of said 0–20 weight percent of paraffins.

21. The process of claim 20, wherein the feed is contacted with component (1) of the catalyst system before it is contacted with component (2) of the catalyst system.

22. The process of claim 21, wherein the catalyst system is a fixed bed catalyst system.

23. The process of claim 22, wherein component (1) and component (2) are in sequential beds in the fixed bed catalyst system.

24. The process of claim 20, wherein said hydrogenative metal is platinum.

25. The process of claim 20, wherein the alpha value of component (1) is 100 to 500.

26. The process of claim 20, wherein the alpha value of component (2) is less than 50.

27. The process of claim 25, wherein the alpha value of component (2) is less than 50.

28. A process for isomerizing a feed which contains an aromatic $C_8$ mixture comprising ethylbenzene and xylenes in which the para-xylene is less than that at thermal equilibrium and which contains 0–20 weight percent paraffins, which process comprises cascading the feed over a catalyst system comprising component (1) and component (2) wherein component (1) comprises ZSM-5 and a metal which is a strong hydrogenation metal, wherein ZSM-5 is characterized by a crystal size, the minimum dimension of which is about at least 1μ, and by an alpha value of at least 100 and wherein the metal comprises 0.05 to 10 weight percent of said component (1), and component (2) comprises ZSM-5 zeolite and a metal which is a strong hydrogenative metal, wherein ZSM-5 has a crystal size less than 1 micron and an alpha value of less than 100, wherein the metal comprises 0.05 to 10 weight percent of the component (2) wherein component (2) comprises at least 50 percent by volume of the catalyst system wherein cascading is undertaken under conditions including a temperature of from about 400° to 1000° F., a pressure of from about 0 to 1000 psig a WHSV of between 0.5 and 100 and a $H_2$/HC molar ratio of between about 0.5 and 10, whereby at least half of the ethylbenzene content of the feed is converted by deethylation and at least one third of said 0–20 weight percent paraffins is hydrocracked.

29. The process of claim 28, wherein said feed is contacted with component (1) before it is contacted with component (2) of the catalyst system.

30. The process of claim 28, wherein the component (1) and component (2) are in sequential beds in a fixed bed catalyst system.

* * * * *